United States Patent
Xing et al.

(10) Patent No.: US 10,526,260 B2
(45) Date of Patent: Jan. 7, 2020

(54) METHOD FOR ADSORPTION SEPARATION OF PROPYLENE AND PROPYNE

(71) Applicant: ZHEJIANG UNIVERSITY, Hangzhou, Zhejiang Province (CN)

(72) Inventors: Huabin Xing, Hangzhou (CN); Xili Cui, Hangzhou (CN); Lifeng Yang, Hangzhou (CN); Zongbi Bao, Hangzhou (CN); Qiwei Yang, Hangzhou (CN); Qilong Ren, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 16/067,576

(22) PCT Filed: May 10, 2017

(86) PCT No.: PCT/CN2017/083730
§ 371 (c)(1),
(2) Date: Jun. 29, 2018

(87) PCT Pub. No.: WO2017/198096
PCT Pub. Date: Nov. 23, 2017

(65) Prior Publication Data
US 2019/0010102 A1    Jan. 10, 2019

(30) Foreign Application Priority Data

May 17, 2016   (CN) .......................... 2016 1 0330278

(51) Int. Cl.
*C07C 7/12* (2006.01)
*B01J 20/22* (2006.01)

(52) U.S. Cl.
CPC ............... *C07C 7/12* (2013.01); *B01J 20/223* (2013.01)

(58) Field of Classification Search
CPC ... C07C 7/12; C07C 11/06; B01J 20/22; B01J 20/223
See application file for complete search history.

(56) References Cited

U.S. PATENT DOCUMENTS

2011/0172412 A1    7/2011   Serre et al.

FOREIGN PATENT DOCUMENTS

| CN | 104492383 | 4/2015 |
| CN | 104525121 | 4/2015 |

OTHER PUBLICATIONS

Janiak et al. (MOFs, MILS and more: concepts, properties and applications for porous coordination networks (PCNs), New J. Chem , 2010, 34, 2366-2388) (Year: 2010).*

(Continued)

*Primary Examiner* — In Suk C Bullock
*Assistant Examiner* — Jason Y Chong
(74) *Attorney, Agent, or Firm* — Jiwen Chen

(57) ABSTRACT

A method for the adsorption separation of propylene and propyne, comprising selectively adsorbing propyne from a mixed gas of propylene and propyne using an anion-containing metal-organic framework material as an adsorbing agent so as to obtain a purified propylene gas. The anion-containing metal-organic framework material is used as an adsorbing agent in the method, and the adsorbing agent is a kind of highly ordered microporous organic-inorganic hybrid material, with the pore size thereof being adjustable within the range of 0.4-1.2 nm, and the pore volume thereof being adjustable within the range of 0.1-1.2 cm3/g. A large number of anionic active sites and a highly ordered spatial arrangement thereof allow the adsorbing agent to exhibit excellent propyne adsorption properties. Thus, the adsorbing agent has a very high propyne selectivity and adsorption volume.

7 Claims, 1 Drawing Sheet

(56) References Cited

OTHER PUBLICATIONS

Nugent et al. ("Porous materials with optimal adsorption thermodynamics and kinetics for $CO_2$ separation" Nature, vol. 495, pp. 80-84, Mar. 7, 2013) (Year: 2013).*

Nugent et al. ("A Robust Molecular Porous Material with High $CO_2$ Uptake and Selectivity" J. Am. Chem. Soc. 2013, 135, 10950-10953) (Year: 2013).*

* cited by examiner

METHOD FOR ADSORPTION SEPARATION OF PROPYLENE AND PROPYNE

This is a U.S. national stage application of PCT Application No. PCT/CN2017/083730 under 35 U.S.C. 371, filed May 10, 2017 in Chinese, claiming priority of Chinese Application No. 201610330278.4, filed May 17, 2016, all of which are hereby incorporated by reference.

FIELD OF THE INVENTION

The present invention relates to a chemical engineering field, and in particular to a method of adsorptive separation of propylene and propyne using metal-organic framework materials.

BACKGROUND

Propylene is the one of the basic raw materials for the production of three major synthetic materials. In industry production, there is about 1.0%~7% propyne existing in the C3 fraction of the oil cracking. Due to the harmful impact of propyne to the propylene polymerization reaction, the concentration of propylene in the propylene gas was required to be below 5 ppm. Nowadays, the newly developed propylene-polymerization catalysts require a much lower concentration of propyne, which is below 1 ppm. The separation and purification of propylene is one of the most important tasks in the petrochemical industry. Otherwise, propyne is an important chemical that has wide applications, it is imperative to efficiently separate propyne.

To removal propyne from propylene, the conventional industrial method is the catalytic selective hydrogenation. The selective hydrogenation technologies mainly includes: C3 gas phase selective hydrogenation, C3 liquid phase selective hydrogenation and catalytic-distillation.

Chinese Patent 85106117.6 disclosed a kind of technology, in which one-stage adiabatic trickle bed reactor was used, and the catalyst used was highly selective. Patent CN102249836A disclosed a method for the preparation of highly selective hydrogenation catalyst. The active component Pd of the catalyst showed specific crystal structure and reactivity, and it can run stably for long period. Patent CN102040446A disclosed the method of employing catalytic distillation, taking advantage of the low concentration of propylene, to reduce the probability of the side-reaction of converting propylene into propane. However, the above described hydrogenation technologies are easy to over-react and then convert propylene into propane. In addition, all these catalysts are noble metals, resulting high costs. Further, the catalysts were easily be poisoned, trace amount of water, carbon monoxide, sulfur chemicals, C4 fractions, arsenic will poison these catalysts. Therefore, it is imperative to control the concentration of trace chemicals, reaction temperature and pressure in the hydrogenation technology, resulting in high cost.

SUMMARY OF THE INVENTION

The present invention provides a method of adsorptive separation of propylene and propyne using metal-organic framework materials containing anions. The inorganic anions in the metal-organic framework materials described herein can selectively adsorb propyne, achieving a deep removal of propyne from propyene/propyne mixtures, thus obtaining the highly pure propyene with extreme low amount of propyne. In addition, the present invention can obtain propyne with high purity, and achieve efficient utilization of propyne.

Metal-organic framework materials are a class of highly ordered crystals with high specific surface area and pore volume. The functional groups, pore size and pore volume can be adjusted by tuning the ligand. In the invention, the metal-organic framework materials contain inorganic and/or organic anions as the adsorption sites, which can selectively adsorb high amount of propyne. Researches have shown that the inorganic/organic anions-containing metal-organic frameworks exhibit higher propyne selectivity and uptake capacity, compared with the conventional metal-organic framework materials. The weak hydrogen bonding between anions and propyne is especially beneficial to the desorption process of propyne. It was found that by tuning the size of the organic ligands, the pore size of the metal-organic framework materials can be adjusted. In addition, interpenetrated structures can adjust the geometry of the pore, and further enhance the adsorption selectivity and uptake capacity.

The disclosure provides a method of separating propyne from propene using metal-organic framework materials, wherein the anion-containing metal-organic framework adsorbents selectively adsorb propyne from propyne/propene mixed gases, thus achieving propene with ultralow amount of propyne.

The obtained propene contain a trace amount of propyne, the concentration of propyne is lower than 1 ppm.

The anion-containing metal-organic framework materials disclosed herein comprises one class of the following four kinds:

The first-class materials were firstly coordinated by metal ion M1 and organic ligand L1, and then bridged by inorganic ligand L2 to form the three-dimensional framework.

In such embodiments, the term "metal ion M1" can comprise one or more of $Zn^{2+}$, $Cu^{2+}$, $Ni^{2+}$, $Co^{2+}$, $Mg^{2+}$, $Al^{2+}$.

The descried "inorganic ligand L2" can comprise one or more of $SiF_6^{2-}$, $TiF_6^{2-}$, $SnF_6^{2-}$, $ZrF_6^{2-}$, $GeF_6^{2-}$.

The descried "organic ligand L1" is selected from any of the following:

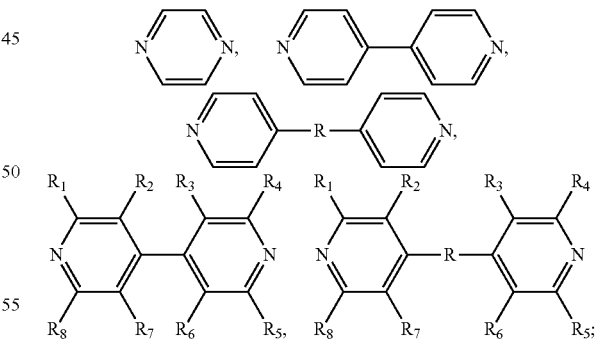

wherein R is selected from any of following groups.

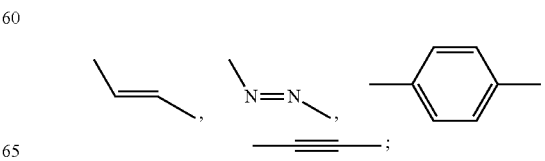

wherein $R_1, R_2, R_3, R_4, R_5, R_6, R_7, R_8$ are selected from the groups H, F, Cl, Br, I, $CH_3$, $NH_2$, OH, $SO_3H$, COOH, $CF_3$.

The second-class materials are porous framework materials formed by metal ions M1 (same as described above), bio-organic ligand L3, and inorganic anions L2 (the same as described above). These described M1, L3, L2 assembled through coordination bond and hydrogen bond.

The descried "organic ligand L3" is selected from any of the following:

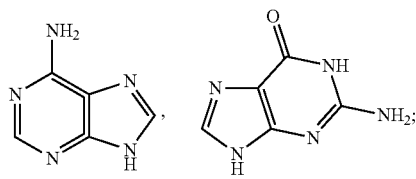

The third class of materials were porous frameworks firstly coordinated by metal ion M1 (the same as descried above) and organic ligand L4, then further coordinated with $Mg(X1)_2$, obtained the metal-organic frameworks with organic anions in the pores.

The descried "organic ligand L4" is selected from any of the following:

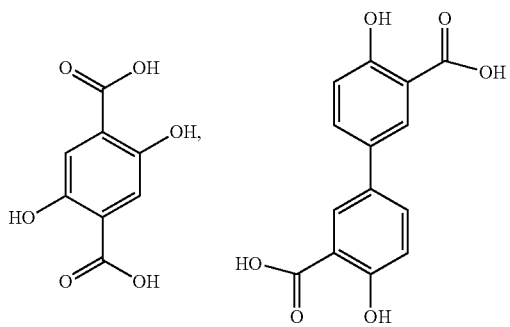 [SMILES: O=C(O)c1cc(O)c(C(=O)O)cc1O ; O=C(O)c1cc(-c2ccc(O)c(C(=O)O)c2)ccc1O]

The descried "organic anion X1" is selected from any of the following:

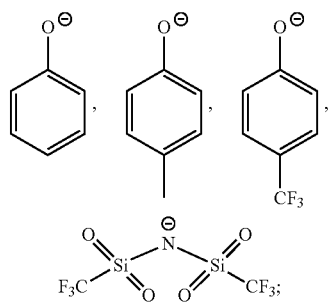

The fourth-class of material were coordinated by metal ion M1 (the same as descried above) and organic ligand L4 (the same as descried above) to form the porous framework materials, and then this material were oxidized to convert divalent metal ion M1 to trivalent, and further by introducing anion X2 to coordinate with trivalent metal ion M1, to maintain the electrical neutrality of the metal-organic material.

The descried "anion X2" is selected from any of the following: $Cl^-$, BC, $I^-$, $COO^-$, $CH_3COO^-$, $NTf_2^-$, $BF_4^-$, $PF_6^-$, $SiF_6^{2-}$, $TiF_6^{2-}$, and $N(CN)_2^-$.

Anion-containing metal-organic framework materials are the first class of materials, among which:

The term "metal ion M1" can comprise one or more of $Zn^{2+}$, $Cu^{2+}$, $Ni^{2+}$.

The descried "inorganic ligand L2" can comprise one or more of $SiF_6^{2-}$, $TiF_6^{2-}$, $SnF_6^{2-}$.

The descried "organic ligand L1" can comprise one or more of pyrazine, 4,4'-dipyridylacetylene, and 4,4'-bipyridine.

When using the first class of materials, the three-dimensional frameworks could be interpenetrated to form interpenetrated structure.

Preferably, L2 is $SiF_6^{2-}$. The anion-containing metal-organic framework materials have been known by the academia as, but not limited to, SIFSIX series or SIFSIX MOFs, including but not limited to, SIFSIX-1-Cu, SIFSIX-2-Cu-i (I=interpenetrated), SIFSIX-3-M1;

Preferably, L2 is $TiF_6^{2-}$. The anion-containing metal-organic framework materials have been known by the academia as, but not limited to TIFSIX series or TIFSIX MOFs, including but not limited to TIFSIX-1-Cu, TIFSIX-2-Cu-i (I=interpenetrated), TIFSIX-3-M1. It was found that the preferred first-class materials have relatively higher pore volume and exhibit excellent adsorption selectivity and capacity of propyne. The first-class materials can be synthesized by the well-known co-precipitation method, interfacial diffusion method, and solvothermal synthesis method.

Anion-containing metal-organic framework materials are the second-class materials, among which:

The term "metal ion M1" can comprise one or more of $Zn^{2+}$, $Cu^{2+}$, $Ni^{2+}$;

The bio-organic ligand L3 is adenine;

The descried "inorganic anion ligand L2" can comprise one or more of $SiF_6^{2-}$ and $TiF_6^{2-}$.

The preferred second-class materials have been known by the academia as, but not limited to MPM-1-TIFSIX. The second-class materials can be synthesized by the well-known co-precipitation method and solvothermal method.

Anion-containing metal-organic framework materials are the third-class or the fourth-class materials, among which:

The descried "metal ion M1" can comprise one or more of $Mg^{2+}$ and $Fe^{2+}$, the descried "organic ligand L4" refers to one or more of 2,5-dihydroxyterephthalic acid, 4,4'-dihydroxy-3,3'-dicarboxylic acid.

The preferred third-class and fourth-class materials have been known by the academia as, but not limited to $M1(dobdc)_2$, or $M1(dobpdc)_2$. The third-class and fourth-class materials can be synthesized by the well-known solvothermal method and interfacial diffusion method.

Anion-containing metal-organic framework materials are the fourth-class of materials, among which the described "anion X2" is selected from any of the following: $Cl^-$, BC, $I^-$, $COO^-$, $CH_3COO^-$.

As described herein, the concentration of propyne in the propyne/propene mixture ranges from 50 ppm to 70%.

As described more fully below, the propyne/propene mixed gases can comprise one or more of propadiene, water, methane, carbon dioxide, carbon monoxide, hydrogen, nitrogen, and other gases. Compared with the conventional catalytic hydrogenation technology, the adsorption technology demonstrated in this disclosure can tolerate various gas impurity, thereby improve the process economics.

It was found that in the described adsorptive separation of propyne and propene using metal-organic framework materials as adsorbent, when propadiene exist in the mixed gases, propadiene can be removed simultaneously by the metal-organic framework materials descried in the present invention.

The physical interactions between the adsorbents described herein and propyne is very weak, and the regeneration is easily. The adsorbent described in this invention was degassed by vacuum desorption, heating vacuum desorption, or heating while blow inert gas. Preferably, the regeneration temperature ranged from 20 to 100° C., while the pressure ranged from 0-1 atm. If the temperature is too high, propyne will easily explode. In addition, if the temperature is too low, the desorption time is relatively long.

An outstanding advantage disclosed in this invention is that it can reach ultra-deep removal of propyne (below 1 ppm), this deep removal of propyne is unprecedented. Both vacuum and heating can reduce the adsorption of propyne on the adsorbent, a better desorption result can be achieved when combine heating method and vacuum together. The desorbed propyne is of high purity, which leads to the efficient use of propyne.

Preferably, the adsorption temperature is between 0-40° C.

The adsorption capacity of propyne in the adsorbent would decrease obviously if the adsorption temperature is over 40° C.

Preferably, the pressure for the adsorption and separation would be 0.5-10 atom.

The adsorption capacity would increase as the pressure rises, however, the over-higher pressure would cause the decrease of the separation selectivity. However, the industrial operating pressure depends on the pressure of the upstream gases.

The shape of the above described adsorbents is particle, pellet, rod, or membrane.

If the above described adsorbent is processed into membranes, the separation of propyne and propene could be realized by membrane separation. When made into other shapes, additives or accessory ingredient could be added according to the need of the particular shape or size.

The outstanding advantages of the present invention are as follows:

1) Using the anion-containing metal-organic framework materials as the adsorbent, the disclosed adsorbents is a kind of highly ordered inorganic-organic hybrid materials with tunable micropore between 0.4-1.2 nm. The pore volume can be tuned between 0.1-1.2 cm$^3$/g. The rich and highly ordered anion binding sites endow the materials with excellent propyne capture property and thus achieve high separation selectivity as well as high adsorption capacity.

2) The interactions between the described metal-organic framework materials and propyne are weak physical interactions, therefore, the desorption process is easy. During the process of the desorptive regeneration of metal-organic framework materials, the absorbed propyne would be collected and the materials could be reused.

3) This disclosure demonstrates the ultra-deep removal of propyne. The content of the propyne in the purified propylene after the adsorption is below 1 ppm, which can meet the most stringent industrial requirement for the downstream polymer-grade propene production.

Therefore, the separation method proposed in the present invention exhibit great potential in the separation and purification of propylene and propyne, showing significant commercial implementation value and economic benefits.

DETAILED DESCRIPTION OF THE EMBODIMENTS

Example 1

Figure 1:
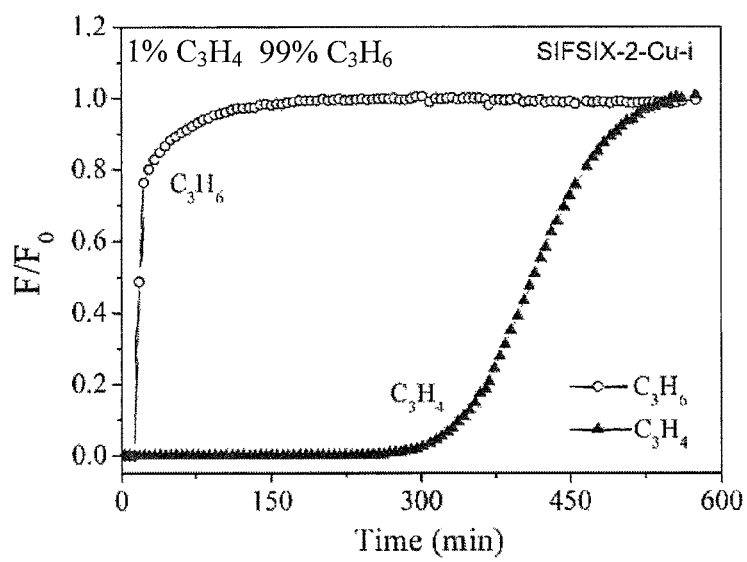
FIG. 1 shows the breakthrough curve of the SIFSIX-2-Cu-i for propylene/propyne (99/1, v/v) separation in the example 1.
Figure 2:
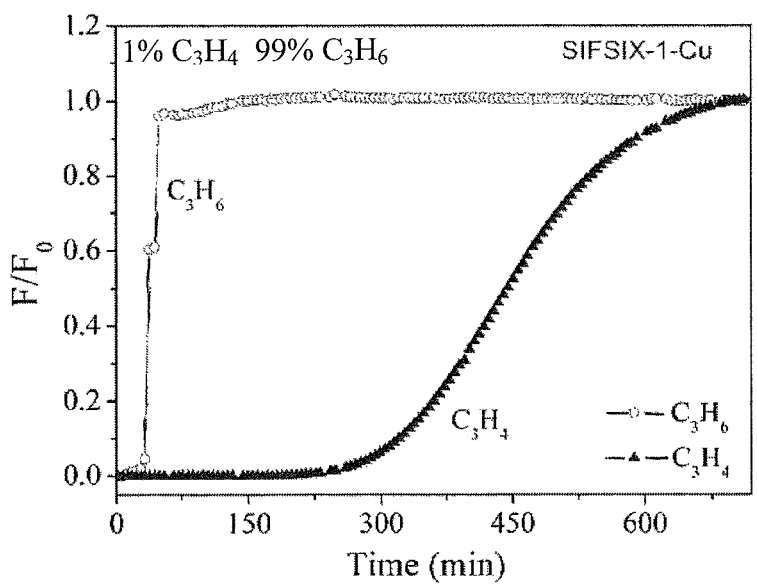
FIG. 2 shows the breakthrough curve of the SIFSIX-1-Cu for propylene/propyne (99/1, v/v) separation in the example 5.

A methanol solution (4.0 mL) of 4,4'-bipyridylacetylene (46.44 mg) was mixed with an aqueous solution (4.0 mL) of 89 mg $Cu(BF_4)_2 \cdot xH_2O$ (metal ion M1) and 45.96 mg $(NH_4)_2SiF_6$ (inorganic anion ligand L2) and then heated at 40-100° C. for 12-36 hours. The obtained SIFSIX-2-Cu-i ($SiF_6^{2-}$ inorganic anion ligand) was further filtered and then immersed in the methanol. The activated adsorbent was loaded into the column (inner diameter 4.6 mm, length 50 mm), the propylene/propyne (99/1, v/v) mixture was introduced into the column at 1.25 mL/min under 25° C. During the first 220 min, propylene only with trace propyne (below 1 ppm) was obtained. The adsorption was stopped. The column with adsorbed propyne was desorbed under vacuum at 50° C. and then could be reused.

Example 2

The column illustrated in the example 1 (inner diameter 4.6 mm, length 50 mm), the propylene/propyne (99/1, v/v) mixture with 1000 ppm $CO_2$ was introduced into the column at 1.25 mL/min under 25° C. During the first 210 min propylene with trace propyne (below 1 ppm) was obtained. The adsorption was stopped. The column with adsorbed propyne was desorbed under vacuum at 30° C. and then could be reused.

Example 3

The column illustrated in the example 1 (inner diameter 4.6 mm, length 50 mm), the propylene/propyne (99/1, v/v) mixture with 2000 ppm water was introduced into the column at 1.25 mL/min under 25° C. During the first 215 min propylene with trace propyne (below 1 ppm) was obtained. The adsorption was stopped. The column with adsorbed propyne was desorbed under vacuum at 80° C. and then could be reused.

Example 4

The column illustrated in the example 1 (inner diameter 4.6 mm, length 50 mm), the propylene with 1000 ppm propyne was introduced into the column at 1.25 mL/min under 40° C. During the first 350 min, propylene with trace propyne (below 1 ppm) was obtained. The adsorption was stopped. The column with adsorbed propyne was purged by He at 60° C.

Example 5

The aqueous solution of 0.28 g $Cu(BF_4)_2 \cdot xH_2O$ (metal ion M1) and 0.199 g $(NH_4)_2SiF_6$ (inorganic anion ligand L2) was added into the glycol solution of 0.35 g 4,4'-bipyridyl (organic ligand L1) and then heated below 100° C. for 2-8 hours. The obtained violet powder SIFSIX-1-Cu ($SiF_6^{2-}$ inorganic anion ligand) was further filtered and then activated. The activated adsorbent was loaded into the column (inner diameter 4.6 mm, length 50 mm), the propylene/propyne (99/1, v/v) mixture was introduced into the column at 1.25 mL/min under 25° C. During the first 180 min, propylene with only with trace propyne (below 1 ppm) was obtained. The adsorption was stopped. The column with adsorbed propyne was desorbed under vacuum at 40° C. and then could be reused.

Example 6

The column illustrated in the example 5 (inner diameter 4.6 mm, length 50 mm), the propylene/propyne (50/50, v/v) mixture was introduced into the column at 1.25 mL/min under 20° C. During the first 65 min, propylene with only with trace propyne (below 5 ppm) was obtained. The adsorption was stopped. The column was purged by He flow under 60° C. for regeneration.

Example 7

The column illustrated in the example 5 (inner diameter 4.6 mm, length 50 mm), the propylene/propyne (90/10, v/v) mixture was introduced into the column at 5 mL/min under 20° C. During the first 25 min, propylene with trace propyne (below 1 ppm) was obtained. The adsorption was stopped. The column were purged by He flow under 60° C. for regeneration.

Example 8

1 mmol $Ni(NO_3)_2$ (metal ion M1), 1 mmol $(NH_4)_2SiF_6$ and 2 mmol pyrazine (organic ligand L1) was added in the 20 mL methanol solution and stirred at 60-80° C. for 2-4 days. The obtained product SIFSIX-3-Ni ($SiF_6^{2-}$ inorganic anion ligand) was further filtered and then activated. Then, the activated adsorbent was loaded into the column (inner diameter 4.6 mm, length 50 mm), the propylene/propyne (99/1, v/v) mixture was introduced into the column at 1.25 mL/min under 25° C. During the first 45 min, only propylene with trace propyne (below 1 ppm) was obtained. The adsorption was stopped. The column with adsorbed propyne was desorbed under vacuum at 60° C.

Example 9

A methanol solution (4 mL) of 46 mg 4,4'-bipyridylacetylene (organic ligand L1) was mixed with an aqueous solution of 89 mg $Cu(BF_4)_2 \cdot xH_2O$ (metal ion M1) and 61 mg $(NH_4)_2TiF_6$ (inorganic anion ligand L2) and then heated below 85° C. for 12 hours. The obtained product TiFSIX-2i-Cu-i ($TiF_6^{2-}$ inorganic anion ligand) was further filtered and then activated. The activated adsorbent was further loaded into the column (inner diameter 4.6 mm, length 50 mm), the propylene/propyne (99/1, v/v) mixture was introduced into the column at 1.25 mL/min under 25° C. During the first 230 min, only propylene with trace propyne (below 1 ppm) was obtained. The adsorption was stopped. The column with adsorbed propyne was desorbed under vacuum at 50° C. and then could be reused.

Example 10

A methanol solution (4 mL) of 46.44 mg 4,4'-bipyridylacetylene (organic ligand L1) was mixed with an aqueous solution of 89 mg $Cu(BF_4)_2 \cdot xH_2O$ (Metal Ion M1) and 69.18 mg $(NH_4)_2SnF_6$ (inorganic anion ligand L2) and then heated below 40-100° C. for 12-36 hours. The obtained product SNFSIX-2-Cu-i ($SnF_6^{2-}$ inorganic anion ligand) was further filtered and then activated. The activated adsorbent was loaded into the column (inner diameter 4.6 mm, length 50 mm), the propylene/propyne (99/1, v/v) mixture was introduced into the column at 1.25 mL/min under 25° C. During first 215 min, only propylene with trace content of propyne (below 1 ppm) was obtained. The adsorption was stopped. The column with adsorbed propyne was desorbed under vacuum at 50° C. and then could be reused Example 11

The aqueous solution of 17.6 mg $Cu(NO_3)_2 \cdot 2.5H_2O$ (metal ion M1) and 15 mg $(NH_4)_2TiF_6$ (inorganic anion ligand L2) was firstly placed in the tube, then an acetonitrile/water (1:1) solution of 20.5 mg adenine (organic ligand L3) was layered on the aqueous solution. The violet crystal MPM-1-TIFSIX was obtained after 4 days (the second kinds of materials described in appended claim). Then, the activated adsorbent was loaded into the column (inner diameter 4.6 mm, length 50 mm), the propylene/propyne (99/1, v/v) mixture was introduced into the column at 1.25 mL/min under 30° C. During the first 50 min, propylene only with low content of propyne (below 20 ppm) was obtained. The adsorption was stopped. The adsorbed propylene was desorbed under vacuum at 50° C.

Example 12

0.59 g of 2,5-dihydroxybenzene-1,4-dicarboxylic acid (organic ligand L4) and 0.24 g $Mg(NO_3)_2 \cdot 9H_2O$ (metal ion M1) were dissolved in the dimethylformamide, ethanol and water mixed solution and heated under 120° C. The obtained product $Mg_2(dobpdc)$ was immersed in the dimethylformamide for 4 days and dried under the vacuum at 180° C. 1.94 g of 4-trifluoromethyl phenol (organic anion X1) was dissolved in the anhydrous triglycol, meanwhile, 8.57 mL tetrahydrofuran with N, N-Diisopropylformamide was dropwise added in anhydrous triglycol. Both the tetrahydrofuran and N,N-Diisopropylformamide were removed after two hours and then the triglycol solution mixed with 125 mg $Mg_2(dobpdc)$, reacting for 7 days at 80° C. The obtained product (the third kinds of materials in the appended claim) was further activated. Then, the activated adsorbent was loaded into the column (inner diameter 4.6 mm, length 50 mm), the propylene/propyne (99/1, v/v) mixture was introduced into the column at 2 mL/min under 25° C. During the first 30 min, only propylene with low content of propyne (below 25 ppm) was obtained. The adsorption was stopped. The adsorbed propylene was desorbed under vacuum at 30° C.

Example 13

1.85 g of 2,5-dihydroxybenzene-1,4-dicarboxylic acid (organic ligand L4), 2.85 g anhydrous $FeCl_2$ (Metal Ion M1), 400 mL dimethylformamide and 50 mL anhydrous methanol were added into the reactor. The kelly product was obtained after stirring for 24 hours at 120° C. Exchange the original solution with fresh anhydrous DMF for several times and finally wash with methanol. The obtained product $Fe_2(dobpdc)$ was dried under the vacuum at 250° C. 13.8 mg of $Fe_2(dobpdc)$ was added into the acetonitrile solution in the glovebox and stirred. 26 mg of $C_{12}H_8S_2PF_6^{2-}$ (inorganic anion X2) was dissolved in the 4 mL acetonitrile and then dropwise added into the above prepared acetonitrile solution and sealed. The product was obtained after 15-24 hours at room temperature. $Fe_2(dobpdc)(PF_6)$ 1.56~5.1MeCN (the fourth kinds of materials in the appended claim). Then, the activated adsorbent was loaded into the column (inner diameter 4.6 mm, length 50 mm), the propylene/propyne (99/1) mixture was introduced to flow into the column at 1.25 mL/min under 25° C. During the first 40 min, only propylene with low content of propyne (below 30 ppm) was obtained. The adsorption was stopped. The adsorbed propylene was desorbed under vacuum at 30° C.

Furthermore, the foregoing descriptions of the embodiments according to the present invention are provided for illustration only, not for the purpose of limiting the invention as defined by the appended claims and their equivalents. Although only the selected embodiments have been chosen to illustrate the present invention, the all involved change or modification without departing from the scope of the invention as defined in the appended claims are covered in this invention.

The invention claimed is:

1. A method of separating propyne from propene using metal-organic framework materials to obtain a propene product with a reduced amount of propyne, comprising selectively adsorbing propyne from a mixed gas comprising propene and propyne using anion-containing metal-organic frameworks as an adsorbent, wherein the anion-containing metal-organic framework materials are selected from first-class materials or second-class materials:
   first-class materials prepared by first coordinating a metal ion M1 and an organic ligand L1 to form two-dimensional frameworks, and then bridging the two-dimensional frameworks by an inorganic ligand L2 to form three-dimensional frameworks, thereby obtaining the first-class materials;
   wherein the metal ion M1 is selected from the group consisting of $Zn^{2+}$, $Cu^{2+}$, $Ni^{2+}$, $Co^{2+}$, $Mg^{2+}$, $Al^{2+}$, and a combination thereof;
   wherein the inorganic ligand L2 is selected from the group consisting of $SiF_6^{2-}$, $TiF_6^{2-}$, $SnF_6^{2-}$, $ZrF_6^{2-}$, $GeF_6^{2-}$, and a combination thereof;
   wherein the organic ligand L1 is selected from any of the following:

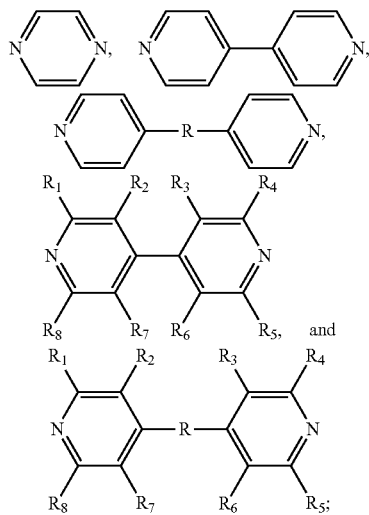

where R is selected from any of the following groups:

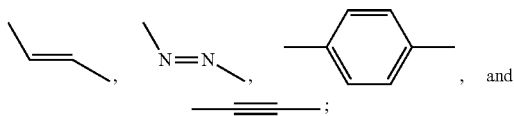

wherein $R_1$, $R_2$, $R_3$, $R_4$, $R_5$, $R_6$, $R_7$, and $R_8$ are each selected from the groups H, F, Cl, Br, I, $CH_3$, $NH_2$, OH, $SO_3H$, COOH, and $CF_3$; and
second-class materials being porous framework materials formed by assembling the metal ion M1, a bio-organic ligand L3, and the inorganic anion L2 through coordination bond and hydrogen bond;
wherein the organic ligand L3 is selected from any of the following:

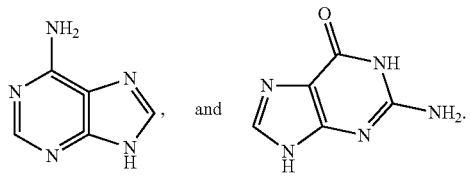

2. The method of separating propyne from propene using metal-organic framework materials according to claim 1, wherein the anion-containing metal-organic framework materials are the first class of materials, among which:
   the metal ion M1 is selected from the group consisting of $Zn^{2+}$, $Cu^{2+}$, $Ni^{2+}$, and a combination thereof;
   the inorganic ligand L2 is selected from the group consisting of $SiF_6^{2-}$, $TiF_6^{2-}$, $SnF_6^{2-}$, and a combination thereof;
   the organic ligand L1 is selected from the group consisting of pyrazine, 4,4'-dipyridylacetylene, 4,4'-bipyridine, and a combination thereof.

3. The method of separating propyne from propene using metal-organic framework materials according to claim 2, wherein the L2 is $SiF_6^{2-}$.

4. The method of separating propyne from propene using metal-organic framework materials according to claim 1, wherein the anion-containing metal-organic framework materials are the second-class materials, among which:
   the metal ion M1 is selected from the group consisting of $Zn^{2+}$, $Cu^{2+}$, $Ni^{2+}$, and a combination thereof;
   the bio-organic ligand L3 is adenine; and
   the inorganic ligand L2 comprises one or more is selected from the group consisting of $SiF_6^{2-}$ and $TiF_6^{2-}$.

5. The method of separating propyne from propene using metal-organic framework materials according to claim 1, wherein a concentration of propyne in the propene product is below 1 ppm, and the regeneration of the adsorbent includes vacuum, heating, or heating with an inert gas flow.

6. The method of separating propyne from propene using metal-organic framework materials according to claim 1, wherein an adsorption temperature is between 0-40° C.

7. The method of separating propyne from propene using metal-organic framework materials according to claim 6, wherein a pressure for the adsorption and separation is 0.5-10 atm.

* * * * *